United States Patent [19]

Granatek et al.

[11] 4,310,515

[45] Jan. 12, 1982

[54] PHARMACEUTICAL COMPOSITIONS OF CISPLATIN

[75] Inventors: Edmund S. Granatek, Syracuse; Gerald M. Ziemba, Bridgeport; Frederick L. Grab, Fayetteville, all of N.Y.

[73] Assignee: Bristol-Myers Company, New York, N.Y.

[21] Appl. No.: 80,857

[22] Filed: Oct. 1, 1979

Related U.S. Application Data

[63] Continuation-in-part of Ser. No. 910,325, May 30, 1978, abandoned.

[51] Int. Cl.³ ............................................. A61K 33/24
[52] U.S. Cl. .................................................... 424/131
[58] Field of Search ....................................... 424/131

[56] References Cited

PUBLICATIONS

Handelman et al., Cancer Therapy Evaluation Program, Div. of Cancer Treatment, National Cancer Ins. (Aug. 1974) pp. 1-5 and 31-32.
Rossoe et al., Cancer 30 pp. 1451-1456 (1972).
Rozencweig et al., Annals of Internal Med., 86 pp. 803-812 (1977).

*Primary Examiner*—Jerome D. Goldberg
*Attorney, Agent, or Firm*—Herbert W. Taylor, Jr.

[57] ABSTRACT

A stable, sterile aqueous solution of cisplatin in a sealed container such as an ampul or vial in unit dosage form suitable for intravenous administration to man is provided which has a concentration of cisplatin between about 0.1 and about 1.0 mgm./ml. and a pH in the range of 2.0 to 3.0 or preferably about 2.5. It can also contain sodium chloride and mannitol.

13 Claims, No Drawings

PHARMACEUTICAL COMPOSITIONS OF CISPLATIN

CROSS-REFERENCE TO RELATED APPLICATION

This application is a continuation-in-part of our prior, copending application Ser. No. 910,325 filed May 30, 1978, now abandoned.

BACKGROUND OF THE INVENTION

1. Field of the Invention

This invention relates to stabilized aqueous solutions of a chemical (cisplatin).

2. Description of the Prior Art

The platinum compounds are a unique group of compounds in the antineoplastic group of agents. They were first noted to have an antibiotic effect by Rosenberg and his colleagues in 1965 and have since been found to be potent antitumor agents in animals.[1,2]

[1] Rosenberg, B., VanCamp, L. and Krigas, T., Inhibition of cell division in *Escherichia coli* by electrolysis products from a platinum electrode. *Nature* (London) 205: 698–699, 1965.
[2] Rosenberg, B., VanCamp, L., Trosko, J. E. and Mansour, V. H., Platinum compounds: A new class of potent antitumor agents. *Nature* (London) 222: 385–386, 1969.

Structurally they represent a complex formed by a central atom of platinum and surrounded by various arrangements of chlorine atoms or ammonia groups in either a cis or trans planar relationship. Two of the more commonly studied platinum compounds are diagrammed below:

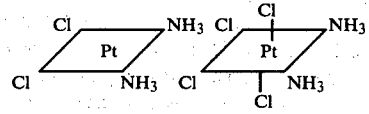

Cis-Platinum (II)  Cis-Platinum (IV)
Diamminedichloride  Diamminetetrachloride

As can be seen, the platinum compound, cis-platinum (II) diamminedichloride, selected for clinical trials by the National Cancer Institute has the chloride and amino groups only in the horizontal plane. The cis form of the diamminedichloride complex has been synthesized according to the following reaction:[3]

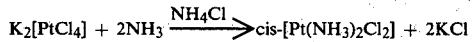

[3] Kauffman, G. B. in J. Kleinberg (Ed.), Inorganic Synthesis, McGraw-Hill Book Co., Inc. New York, 1963.

The National Cancer Institute has been conducting clinical trials in cancer chemotherapy of the chemical for which the United States Adopted Name (USAN) is now cisplatin. Certain information regarding its chemistry and its pharmaceutical formulation are given in the publication titled Clinical Brochure, CIS-PLATINUM (II) DIAMMINEDICHLORIDE (NSC-119875), H. Handelman et al., Investigational Drug Branch, Cancer Therapy Evaluation Program, Division of Cancer Treatment, National Cancer Institute (Revised, August, 1974), on pages 1–5 and 31–32. The last two pages of Handelman et al. concern the formulation of cisplatin supplied gratis by the N.C.I. to clinicians for their clinical evaluation in the chemotherapy of cancer and read as follows:

PHARMACEUTICAL DATA SHEET

NSC-119875    Cis-Diamminedichloroplatinum (II)

Dosage Formulation 10 mg./vial: The contents of each 20 ml. flint vial appears as an off-white lyophilized cake. Each vial contains 10 mg. of NSC-119875; 90 mg. of Sodium Chloride; 100 mg. of Mannitol and Hydrochloric acid for pH adjustment.

Solution Preparation 10 mg./vial: When reconstituted with 10 ml. of Sterile Water for Injection, USP, each ml. of the resulting solution will contain 1 mg. of NSC-119875, 10 mg. of Mannitol, and 9 mg. of Sodium Chloride having a pH range of 3.5–4.5.

Storage: The dry, unopened vials should be stored at refrigeration temperatures (4°–8° C.).

Stability: Intact vials have a provisional stability of one year when stored at refrigeration temperature (4°–8° C.). Stability recommendations may be adjusted pending completion of a two-year shelf-life study. Reconstitution as recommended results in a pale, yellow solution which is stable for not more than one hour at room temperature (22° C.) when exposed to normal room illumination and not more than eight hours at room temperature (22° C) when protected from light. Reconstituted solutions may form a precipitate after one hour at refrigeration temperature (4°–8° C.).

Caution: The lyophilized dosage formulations contain no preservatives and therefore it is advised to discard solutions eight hours after reconstitution.

August, 1974
Clinical Drug Distribution Section
Drug Development Branch

Mention of this formulation and additional information on its clinical use is given, for example, in Cancer Chemotherapy Reports, Part 1, Vol. 57, No. 4, pages 465–471 (1973).

Cancer 30: 1451–1456 (1972) in reference to cisplatin states that

"The drug material used in this study was manufactured by Ben Venue Laboratories Inc., Bedford, Ohio. It was supplied by the Cancer Therapy Evaluation Branch of the National Cancer Institute in vials containing 10 mg. of cis-diamminedichloroplatinum, 10 mg. (sic) of mannitol and 9 mg. (sic) of NaCl. The resulting yellowish white powder dissolved readily in 8–10 ml. of sterile water and was injected immediately after preparation."

Annals of Internal Med. 86: 803–812 (1977) refers to cisplatin as "DDP" and states that "The drug DDP is presently available as an investigational drug only to qualified specialists through the Investigational Drug Branch of the Cancer Therapy Evaluation Program, National Cancer Institute. The product is supplied as a white lyophylized powder in vials containing 10 mg. of DDP, 90 mg. of sodium chloride, 100 mg. of mannitol (U.S.P.), and hydrochloric acid for pH adjustment. When reconstituted with 10 ml. of sterile water for injection (U.S.P.), each ml. of the resulting solution will contain 1 mg. of DDP, 10 mg. of mannitol, and 9 mg. of NaCl. The pH of the resulting solution will be 3.4 to 4.5. At 22° C., the reconstituted solution is stable for at least 8 h."

Thus the formulations described above are stated to require refrigeration (4°-8° C.) while in vials in the solid state (i.e., before reconstitution), they are difficult to reconstitute and they have a useful life of only about twenty hours at room temperature (22° C.) following reconstiution. The very act of reconstitution can cause problems if improperly performed and is better avoided. In addition, because the aqueous solubility of cisplatin is only about 1 mgm./ml., the cost of preparing dosage forms containing more than 25 mgm./vial by lyophilization becomes prohibitive.

It was the object of the present invention to provide a stable, therapeutically acceptable, intravenously injectable dosage form of cisplatin which would not require lyophilization and reconstitution, which would not require refrigeration during shipment and storage, and which could be supplied in dosages of 50 mg. or larger.

These objectives were achieved by the present invention as described in detail below.

SUMMARY OF THE INVENTION

There is provided by the present invention a stable, sterile aqueous solution of cisplatin in a sealed container such as an ampul or vial in unit dosage form suitable for intravenous administration to man, said solution having a concentration of cisplatin between about 0.1 and about 1.0 mgm./ml. and preferably of about 1.0 mgm./ml. and a pH in the range of 2.0 to 3.0 and preferably in the range of 2.3 to 2.7 and most preferably a pH of about 2.5, said pH being caused by the presence of the appropriate amount of a nontoxic, pharmaceutically and therapeutically acceptable acid, said acid preferably being a strong mineral acid and most preferably being hydrochloric acid; said solution optionally containing in addition a nontoxic, pharmaceutically acceptable, inorganic source of chloride ions in a concentration equivalent to that produced by the presence of sodium chloride in a concentration in the range of 1 to 20 mgm./ml. and most preferably about 9 mgm./ml.; said solution optionally also being either free of any other added chemicals or also containing a customary, harmless, physiologically acceptable excipient, which is preferably mannitol, in a concentration in the range of 2 to 150 mgm./ml. and preferably a concentration of about 10 mgm./ml., said solution exhibiting less than 10% (and usually less than 4%) loss of potency as measured by high performance liquid chromatography (HPLC) upon storage for three months at 56° C. Preservatives can be added if desired.

DESCRIPTION OF THE PREFERRED EMBODIMENTS

EXAMPLE 1
Cisplatin Injection 1 Mg./Ml.
[1 Mg. Cis-diamminedichloroplatinum (II) per 1 Ml.]
Formula

|  | Per Ml. | Per Liter |
|---|---|---|
| Cis-diamminedichloro-platinum (II) | 0.0010 g.[A] | 1.000 g.[A] |
| Sodium Chloride, U.S.P. | 0.0090 g. | 9.000 g. |
| Mannitol, U.S.P. | 0.0100 g. | 10.000 g. |
| Hydrochloric Acid, Conc. U.S.P. | q.s. to pH 2.0–3.0[B] | q.s. to pH 2.0–3.0[B] |
| Water for Injection, | | |

-continued
EXAMPLE 1
Cisplatin Injection 1 Mg./Ml.
[1 Mg. Cis-diamminedichloroplatinum (II) per 1 Ml.]
Formula

|  | Per Ml. | Per Liter |
|---|---|---|
| U.S.P. | q.s. 1.0 Ml. | q.s. 1000.0 Ml. |

NOTES:
[A]100% basis, adjust weight based on reported purity to provide 1.0 g. 100% cis-diamminedichloroplatinum (II) per liter.
[B]Approximately 0.035–0.050 ml. of 37% hydrochloric acid required per gram of sodium chloride to obtain a pH of approximately 2.5.

PRECAUTIONS

Cis-diamminedichloroplatinum (II) is a toxic substance and is listed on page 942 in the 1976 edition of the "Registry of Toxic Effects of Chemical Substances." The OSHA Standard of Time Weighted Average (TWA) is 2 mcg./m$^3$. Consult the above, listed references, pertinent local publications and regulations and such publications as the National Cancer Institute Safety Standards for Research Involving Chemical Carcinogens and the National Institute of Health Specifications for a Class II type 1 Safety Cabinet. Any cis-diamminedichloroplatinum (II) weighing, the working surface of the batching vessel, the filling, stoppering, and sealing must be provided with such protection.

All personnel involved with compounding of this product must be protected with full nylon head/face cover, coveralls, rubber gloves and a respirator equivalent to the MSA Ultra Filter Respirator rated for environments contaminated with dusts, fumes and mists having a TWA rating of less than 50 mcg./m$^3$. During the sterile liquid filling the sterile head/face cover, surgeon's gauze mask and goggles can replace the respirator. Any uniforms grossly contaminated due to spills, etc. should be stored in a closed metal container until burned.

*The importance of protecting personnel during the handling, manufacturing and assaying of this product in accordance with the above cannot be overemphasized.*

The prime bulk cis-diamminedichloroplatinum (II) must be protected from light. The processing and filling of vials described herein was conducted under diffused natural/fluorescent light.

EQUIPMENT

Batching Vessel

Glass-lined, agitated, pressure vessel. A 316 SS agitator is permissible. Working volume must be consistent with batch size. A dipstick and calibration curve of tank volume is required for determining volume.

Millipore Membrane Filter Holders

316 SS. Filter area with necessary pre-filters and 0.22 micron final sterilizing filter.

Transfer Hoses

Teflon or Tygon.

All stainless steel contacts should meet 316 SS requirements. All other equipment should be appropriate to produce a sterile, non-pyrogenic, particulate-free product.

Manufacturing Instructions

A. These instructions are written for an eight-hour batching to filling operation. Storage of this product before filling has not been investigated at this writing.

B. Maintain 27° C.±2° C. temperature conditions throughout entire batching and filtering operations.

1. Place 80% of the batch volume of Water for Injection, U.S.P. in a suitable vessel.

2. With agitation add the sodium chloride. Agitate ten minutes or until dissolved.

3. With good agitation carefully adjust the pH of the sodium chloride solution to 2.0–3.0 (preferably 2.5) with concentrated hydrochloric acid. See estimated amount under note "B" formula sheet. Agitate for ten minutes after last addition. Recheck pH.

4. With good agitation add the mannitol and agitate ten minutes or until dissolved.

5. With good agitation and taking special precautions against dusting and exposure, add the cis-diamminedichloroplatinum (II). Rinse its container sufficiently with an approproate amount of water for injection and add to the batch.

6. Agitate until completely dissolved. Approximately 60–90 minutes will be required for complete dissolution. Monitor pH and add additional concentrated hydrochloric acid if required to maintain at 2.0–3.0 (optimum 2.5).

7. Carefully adjust volume to theoretical batch volume with water for injection. Make final pH check.

8. Pass the solution through a clean, sterile 0.22 micron Millipore Filter into the sterile filling line.

9. Fill as directed below for the following products:

10 Mg./Vial

Sterile, Type I amber, 15 ml. vial, with a 10-ml. fill. Stopper with red, 20 mm Teflon-faced stoppers and seal with aluminum seals. Numbered as K93, 100 and 107 with nitrogen overlay and K94, 101 and 108 without nitrogen overlay.

25 Mg./Vial

Sterile, Type I amber, 50 ml. vial with a 25-ml. fill. Stopper with red, 20 mm Teflon-faced stoppers and seal with aluminum seals. Numbered as K95, 102 and 109 with nitrogen overlay and K96, 103 and 110 without nitrogen overlay.

50 Mg./Vial

Sterile, Type I amber, 50 ml. vial with a 50-ml. fill. Stopper with red, 20 mm Teflon-faced stoppers and seal with aluminum seals. Numbered as K97, 104 and 111 with nitrogen overlay and K98, 105 and 112 without nitrogen overlay.

Original potencies by HPLC assay were in the range of 0.99 to 1.00 mgm./ml.

These formulations after storage at 45° C. and 56° C. were examined for loss of potency and pH with the results tabulated below.

The percentage loss in potency after storage for one, three and/or four months at the indicated temperature was found by HPLC assay to be as follows:

|  | Percentage Loss in Potency | | | | |
|---|---|---|---|---|---|
|  | 56° C. | | | 45° C. | |
|  | One Month | Three Months | Four Months | One Month | Four Months |
| K93 | 4.0 |  | 6.0 |  | −1.0* |
| K94 | 2.0 | 6.0 | 5.0 |  | −2.0* |
| K95 | 0.0 |  | 2.0 | −1.0* | −2.0* |
| K96 | 1.0 | 8.0 | 4.0 | 0.0 | −2.0* |
| K97 | 4.0 |  | 6.0 |  | 2.0 |
| K98 | 4.0 | 8.0 | 7.0 |  | 2.0 |
| K100 | 3.0 |  | 4.0 |  | −2.0* |
| K101 | 3.0 | 4.0 | 4.0 |  | −3.0* |
| K102 | 3.0 |  | 8.1 |  | 1.0 |
| K103 | 5.1 | 3.0 | 6.1 |  | 2.0 |

-continued

|  | Percentage Loss in Potency | | | | |
|---|---|---|---|---|---|
|  | 56° C. | | | 45° C. | |
|  | One Month | Three Months | Four Months | One Month | Four Months |
| K104 | 0.0 |  | 5.1 | −1.0* | 1.0 |
| K105 | 0.0 | 3.0 | 3.0 | 0.0 | −1.0 |
| K107 | 1.0 |  | 5.1 | 0.0 | −3.0* |
| K108 | 2.0 | 3.0 | 5.1 | 1.0 | −3.0* |
| K109 | 3.0 |  | 4.0 |  | −3.0* |
| K110 | 3.0 | 4.0 | 6.1 |  | −1.0* |
| K111 | 7.1 |  | 13.1 |  | 3.0 |
| K112 | 7.1 | 9.1 | 9.1 |  | 3.0 |

*Negative sign means assay showed an increase in potency.

The absence of a figure for loss of potency means that no assay was performed on that lot at that time.

| pH STABILITY, CISPLATIN INJECTION, 1 MG./ML. | | | | | | |
|---|---|---|---|---|---|---|
|  | ORIG. | 1 MON. 56° C. | 2 MON. 56° C. | 3 MON. 56° C. | 4 MON. 56° C. | 4 MON. 45° C. |
| 10 MG./VIAL |  |  |  |  |  |  |
| 78K93 (N₂↑) | 2.40 | 2.70 | 2.40 | 2.50 | 2.50 | 2.45 |
| 78K94 | 2.40 | 2.70 | 2.40 | 2.60 | 2.30 | 2.40 |
| 78K100 (N₂↑) | 2.40 | 2.65 | 2.40 | — | 2.50 | 2.40 |
| 78K107 (N₂↑) | 2.40 | 2.70 | 2.40 | — | 2.50 | 2.50 |
| 78K108 | 2.40 | 2.65 | 2.40 | 2.65 | 2.50 | 2.50 |
| 25 MG./VIAL |  |  |  |  |  |  |
| 78K95 (N₂↑) | 2.40 | 2.45 | 2.35 | — | 2.50 | 2.50 |
| 78K96 | 2.40 | 2.50 | 2.30 | 2.55 | 2.50 | 2.45 |
| 78K102 (N₂↑) | 2.40 | 2.50 | 2.30 | — | 2.40 | 2.45 |
| 78K103 | 2.40 | 2.50 | 2.35 | 2.60 | 2.40 | 2.45 |
| 78K109 (N₂↑) | 2.40 | 2.50 | 2.30 | — | 2.45 | 2.40 |
| 78K110 | 2.40 | 2.50 | 2.35 | 2.60 | 2.50 | 2.45 |

|  | ORIG. | 1 MON. 56° C. | 2 MON. 56° C. | 3 MON. 56° C. | 4 MON. 56° C. | 4 MON. 56° C. |
|---|---|---|---|---|---|---|
| 50 MG./VIAL |  |  |  |  |  |  |
| 78K97 (N₂↑) | 2.40 | 2.40 | 2.30 | — | 2.45 | 2.40 |
| 78K98 | 2.40 | 2.45 | 2.30 | 2.55 | 2.40 | 2.40 |
| 78K104 (N₂↑) | 2.40 | 2.50 | 2.35 | — | 2.45 | 2.40 |
| 78K105 | 2.45 | 2.50 | 2.40 | 2.60 | 2.45 | 2.40 |
| 78K111 (N₂↑) | 2.50 | 2.55 | 2.40 | — | 2.50 | 2.50 |
| 78K112 | 2.50 | 2.55 | 2.40 | 2.65 | 2.50 | 2.45 |

The above-described solutions, with and without nitrogen cover, thus have shown 7% or less loss in potency after storage for one month at 56° C. and 45° C. with the majority showing a loss of potency of 3% or less. The pH of the solutions remained between 2.4 and 2.7.

Physically, no change is apparent at 56° C. or 45° C. after one month. Solutions remain clear and colorless.

One sample at each temperature station for all products was tested inverted exposing the solution to the Teflon-coated plug stopper. Samples from inverted products were assayed from 56° C. at one month with and without N₂↑ exposure. Stability was not affected at one month 56° C. as samples showed only 1–2% loss of potency.

At two weeks 4° C. samples were observed for crystallization of cis-diamminedichloroplatinum (II). No crystals were observed until one month and it was only noted randomly, not in every sample. Only one lot of the 10 mg./vial and 25 mg./vial products show some crystals forming randomly at 4° C. Crystallization is noted throughout all lots of 50 mg./vial products but again not in all samples. One sample from 4° C. with crystals could not be redissolved by warming the solution to 37° C. with agitation. Only partial success was obtained. It appears these products cannot be stored under refrigerated conditions as even redissolving of crystallized products was difficult.

An experiment was performed to determine the stability with respect to pH and potency as determined by HPLC assay of the preferred formulations of the present invention and an otherwise identical formulation having a higher original pH, that is, pH 3.5. Details of the procedures and results are set forth below.

The study was conducted to determine the pH stability profile of Cisplatin injections 1 mg./ml. in 10 mg. vials with the following formula:

|  | Per Ml. |
| --- | --- |
| Cis-Diamminedichloroplatinum (II) | 0.001 g. |
| Mannitol, U.S.P. | 0.010 g. |
| Sodium Chloride, U.S.P. | 0.009 g. |
| Hydrochloric Acid (0.1N and 5.0N) | q.s. to pH 2.0 to 3.5 |
| Deionized Water | q.s. to 1.0 Ml. |

For this study, eight lots were prepared adjusting the pH in a range of pH 2.0 to 3.5. More specifically, at pH 2.0, 2.5, 2.6, 2.7, 2.8, 2.9, 3.0 and 3.5. This formula is identical to the formula described above with the exception of the normality of the Hydrochloric Acid used for the expansion of the pH range and Deionized Water in place of Water for Injection, U.S.P. These lots were agitated for 30 minutes to ensure proper pH values before placing under stability test without a Nitrogen overlay. The following table identifies the eight lots, their initial (original) pH values and their pH values after storage at 56° C.:

| | pH Values | | | | |
| --- | --- | --- | --- | --- | --- |
| Lot | Original | 2 Wks. 56° C. | 1 Mo. 56° C. | 2 Mos. 56° C. | 3 Mos. 56° C. |
| 79K34 | 2.0 | — | 2.0 | 2.0 | 2.0 |
| 79K95 | 2.5 | 2.5 | 2.6 | 2.5 | 2.6 |
| 79K94 | 2.6 | 2.6 | 2.7 | 2.7 | 2.8 |
| 79K93 | 2.7 | 2.7 | 2.8 | 2.9 | 3.0 |
| 79K92 | 2.8 | 2.8 | 3.0 | 3.1 | 3.2 |
| 79K91 | 2.9 | 3.0 | 3.2 | 3.3 | 3.6 |
| 79K35 | 3.0 | — | 3.3 | 3.8 | 4.0 |
| 79K90 | 3.5 | 4.4 | 5.2 | 6.3 | 6.2 |

Potency

The potency after storage of these solutions up to three months at 56° C. was determined by HPLC analysis. This assay has a ±2% variability and the results are listed below. Initial potencies for these solutions ranged from 0.93 mg./ml. to 1.01 mg./ml. The following table indentifies the eight lots and their percent change in potency at 56° C.

| | Percentage Change in HPLC Potency | | | | |
| --- | --- | --- | --- | --- | --- |
| Lot | Original pH | 2 Wks. 56° C. | 1 Mo. 56° C. | 2 Mos. 56° C. | 3 Mos. 56° C. |
| 79K34 | 2.0 | —% | −1.1% | −4.3% | −7.5% |
| 79K95 | 2.5 | −3.0 | −0.0 | −5.1 | *−7.1 |
| 79K94 | 2.6 | −1.0 | +3.1 | −1.0 | −3.1 |
| 79K93 | 2.7 | −2.0 | 0.0 | 0.0 | 0.0 |
| 79K92 | 2.8 | −2.0 | −1.0 | −4.0 | −4.0 |
| 79K91 | 2.9 | −1.0 | 0.0 | −2.0 | −3.0 |
| 79K35 | 3.0 | — | −3.0 | −4.0 | −6.0 |
| 79K90 | 3.5 | −2.0 | −4.0 | −10.0 | −14.0 |

*These results are the average of two assays.

In addition, a study was conducted to determine the stability of Cisplatin solutions not containing mannitol and having the following formula:

|  | Per Ml. |
| --- | --- |
| Cis-Diamminedichloroplatinum (II) | 0.001 g. |
| Sodium Chloride, U.S.P. | 0.009 g. |
| Hydrochloric Acid | q.s. to pH 2.3 or 2.4 |
| Deionized Water | q.s. to 1.0 Ml. |

These lots were agitated for thirty minutes to ensure proper pH values before placing under stability test with or without a nitrogen overlay. They were filled at the rate of 10 ml. (i.e. 10 mg. of cisplatin) in 15 cc. vials or either 25 or 50 mg. in 50 ml. vials. All vials were amber glass, 20 mm. "Teflon" coated, No. 541 red stoppers with aluminum seal. The lots were as follows:

| | Nitrogen Overlay | Original pH |
| --- | --- | --- |
| Lot 78K257 - 10 Mg./Vial | With | 2.4 |
| Lot 78K258 - 10 Mg./Vial | Without | 2.4 |
| Lot 78K440 - 25 Mg./Vial | With | 2.4 |
| Lot 78K441 - 25 Mg./Vial | Without | 2.4 |
| Lot 78K445 - 50 Mg./Vial | With | 2.3 |
| Lot 78K446 - 50 Mg./Vial | Without | 2.3 |

Potency

The potency after storage of these solutions up to four months at 56° C. was determined by HPLC analysis and the results are listed below. Initial potencies for these solutions ranged from 0.96 mg./ml. to 0.98 mg./ml. The following table identifies the six lots and their percent change in potency at 56° C.

| | Percentage Loss in HPLC Potency at 56° C. | | | |
| --- | --- | --- | --- | --- |
| Lot | 1 Mo. | 2 Mos. | 3 Mos. | 4 Mos. |
| 78K257 | 2.1 | 4.2 | 4.2 | 10.4 |
| | | | | 7.3 |
| 78K258 | 3.1 | 5.2 | 6.2 | 11.3 |
| | | | | 8.2 |
| 78K440 | 7.1 | 2.0 | 9.2 | 11.2 |
| | | | | 10.2 |
| 78K441 | 3.1 | 2.0 | 6.1 | 10.2 |
| | | | | 10.2 |
| 78K445 | 3.1 | 4.1 | 5.1 | 8.2 |
| | | | | 5.1 |
| 78K446 | 0.0 | 3.1 | 8.2 | 10.3 |
| | | | | 8.2 | 9.3 |

| Lot | pH Values (56° C.) | | | | |
|---|---|---|---|---|---|
| | Original | 1 Mo. | 2 Mos. | 3 Mos. | 4 Mos. |
| 78K257 | 2.4 | 2.5 | 2.4 | 2.5 | 2.6 |
| 78K258 | 2.4 | 2.5 | 2.5 | 2.5 | 2.6 |
| 78K440 | 2.4 | 2.5 | 2.4 | 2.4 | 2.4 |
| 78K441 | 2.4 | 2.5 | 2.4 | 2.4 | 2.5 |
| 78K445 | 2.3 | 2.4 | 2.3 | 2.4 | 2.4 |
| 78K446 | 2.3 | 2.4 | 2.4 | 2.4 | 2.4 |

Comparison Study

The data below document the reconstituted stability of a lot of lyophilized Cisplatin which was prepared by Ben Venue Laboratory.

Cis-Platinum Injection (77L211) was reconstituted with 10 ml. of Sterile Water for Injection, U.S.P. to yield a concentration of 1 mg./ml. and then placed on stability testing in the original Wheaton S-205, 20 cc., Type I amber vial with a West 541 red Teflon coated 20 mm. stopper—Experiment No. 77K946 was assigned to the reconstituted sample.

These data confirm the instability of the reconstituted pH 4.3 lyophilized Cisplatin formulation with respect to both pH and chemical integrity.

LOT 77K946,
CISPLATIN, 10 MG./VIAL (BEN VENUE LOT #BVP33)
RECONSTITUTED STABILITY
1 MG./ML. IN STERILE WATER FOR INJECTION

| | 56° C. | | | 45° C. | | |
|---|---|---|---|---|---|---|
| | pH | Potency (Mg./Ml.) | Percent Change In Potency | pH | Potency (Mg./Ml.) | Percent Change In Potency |
| Original | 4.30 | 0.99 | — | 4.30 | 0.99 | — |
| 2 Weeks | 5.60 | 1.06 | +7.1 | 5.40 | 0.96 | −3.0 |
| 1 Month | 6.50 | 0.88 | −11.1 | 5.70 | 0.92 | −7.1 |
| 2 Months | 6.50 | 0.80 | −19.2 | 6.50 | 0.84 | −15.2 |
| 3 Months | 6.70 | 0.75 | −24.2 | 6.70 | 0.84 | −15.2 |

| | 37° C. | | | 25° C. | | |
|---|---|---|---|---|---|---|
| | pH | Potency (Mg./Ml.) | Percent Change In Potency | pH | Potency (Mg./Ml.) | Percent Change In Potency |
| Original | 4.30 | 0.99 | — | 4.30 | 0.99 | — |
| 1 Month | — | 1.02 | +3.0 | — | — | — |
| 2 Months | 5.60 | 0.95 | −4.0 | — | — | — |
| 3 Months | 6.60 | 0.86 | −13.1 | — | — | — |
| 4 Months | 6.70 | 0.85 | −14.1 | — | — | — |
| 5 Months | 6.70 | 0.86 | −13.1 | — | — | — |
| 6 Months | — | — | — | 5.3 | 1.04 | +5.1 |

Cis-platinum (II) diamminedichloride (NSC 119875) is an inorganic compound first noted to prevent replication of E. coli and subsequently found to possess antitumor activity. The drug exerts it effects of interfering with DNA synthesis by causing cross-linking of complementary strands of DNA. It has activity in a variety of tumor systems including L1210, Sarcoma 180, Walker 256 carcinosarcoma, DMBA induced mammary tumors and ascitic B16 melanosarcoma. The compound is especially interesting in that it exhibits synergism with a large number of currently-used chemotherapeutic agents. Large animal toxicology studies showed renal tubular necrosis, enterocolitis, bone marrow hypoplasia and lymphoid atrophy. Phase I studies have demonstrated the following toxicities: myelosuppression, renal insufficiency, high frequency ototoxicity and GI intolerance. Currently used dosages with mild to moderately acceptable toxicity are in the range of 60–100 mg/m² IV as a single dose or divided over 3–5 days, to be repeated at four-week intervals.

The solutions of the present invention are used in the same manner and for the same purpose as stated above and in the other publications and in the voluminous medical literature on this subject. As stated therein, frequent use is made of concurrent therapy with other chemotherapeutic agents for best results. When desired, the solutions of the present invention may be added immediately before use to a sterile, pharmaceutically acceptable aqueous diluent such as glucose or saline. Administration is either by direct intravenous injection or by intravenous infusion.

High Performance Liquid Chromatography (HPLC)
Assay for cis-Diamminedichloroplatinum.

Method

Cis-diamminedichloroplatinum is chromatographed on a Water's $\mu$-Bondapak-NH$_2$ column using a loop injection technique. Detection is achieved by monitoring the U.V. absorbance at 313 nm and quantitation is accomplished by peak height measurement with external calibration. This method is applicable to bulk powders and solid dose formulations containing NaCl and mannitol. Specificity has been demonstrated by separation of the cis and trans isomers and apparent degradations (moisture, acid, base, heat and accelerated light).

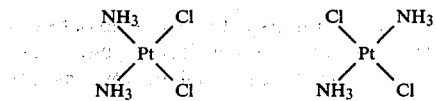

Cis-(NH$_3$)$_2$ Cl$_2$ Pt II     Trans-(NH$_3$)$_2$ Cl$_2$ Pt II

HPLC Conditions

Column—Water's Micro-Bondapak-NH$_2$ (300 MM×4.0 MM ID) 027386 or equivalent.
Mobile Phase—Ethyl acetate/methanol/dimethylformamide/distilled water (25/16/5/5). Use Burdick and Jackson distilled in glass spectroquality reagents. Degas the water prior to use and the solution after mixing.
Detector—Water's Model 440 Absorbance Detector.
Wavelength—313 nm (U.V.).
Sensitivity—0.1 AUFS.
Injector—A 20 microliter loop injector.
The Loop Injector—A Valco 7000 psi stainless steel valve (CV-6-UHPa-C20).
Injection Volume—20 microliter.
Solvent Delivery System—Water's Model 6000A pump.
Flow—2.0 ml./minute.
Retention—2.8 minutes (approx.).
Recorder—Heath Model SR-255B.
Chart Speed—0.5 inch/min.
Range—10 millivolt.

HPLC Analysis

Using the conditions above, obtain chromatograms of the standard and sample preparations in duplicate.
Reference Standard of cis-diamminedichloroplatinum (DDP):
Lot No.=78F7 (Matthey Bishop Lot No. AM7702)

Assigned Purity=99.8%

Solvents—Burdick and Jackson (distilled in glass) spectroquality.

Standard—Weigh accurately 25 mg. of cis-diamminedichloroplatinum (DDP) into a 25-ml. volumetric flask. Dissolve in and dilute to volume with dimethylformamide.

Lyophilized Injection—Reconstitute vial contents with 10.0 ml. of dimethylformamide and mechanically shake for 5 minutes (alternately a sonic bath may be used for 2 minutes). Filter 5.0 ml. of the sample solution (Millipore Filter Kit or equivalent) discarding the first ml.

Content Uniformity—Prepare 10 vials as described above and assay.

Calculations $$\text{STANDARD FACTOR } (SF) = \frac{\text{MG. STANDARD/ML.}}{\text{AVERAGE PEAK HEIGHT STANDARD}}$$

$$\text{MG. DDP/GRAM} = \frac{SF \times \text{AVERAGE PEAK HEIGHT SAMPLE} \times 25}{\text{WT. SAMPLE (GM.)}}$$

MG. DDP/VIAL =
   $SF \times$ AVERAGE PEAK HEIGHT SAMPLE $\times$ 10

For assay, average results obtained for 10 vials from content uniformity test.

Method

The method of assay for cisplatin described above is applied to aqueous solutions (dose formulations) containing NaCl and mannitol after making the changes indicated below.

HPLC Conditions

Mobile Phase—Acetonitrile/distilled water (75/25, v/v).

Use Burdick and Jackson distilled in glass spectroquality reagents. Degas the water prior to use and the solution after mixing.

Injector—A 100 microliter loop injector.

Injection Volume—100 microliter.

Retention—2.0 minutes (approx.).

HPLC Analysis

Standard—Weigh accurately 25 mg. of cis-diamminedichloroplatinum (DDP), 225 mg. sodium chloride and 250 mg. mannitol into a 25-ml. volumetric flask. Dissolve in and dilute to volume with distilled water. Pipet 5.0 ml. of the resulting solution into a 25.-ml. volumetric flask, add 2.0 ml. of distilled water and take to volume with acetonitrile.

Sample (1 mg./ml.)—Pipet 5.0 ml. of the sample into a 25-ml. volumetric flaks, add 2.0 ml. of distilled water and take to volume with acetonitrile.

Calculations $$\text{STANDARD FACTOR } (SF) = \frac{\text{MG. STANDARD/ML.}}{\text{AVERAGE PEAK HEIGHT STANDARD}}$$

MG. DDP/ML. =
   $SF \times$ AVERAGE PEAK HEIGHT SAMPLE $\times$ 25

This invention is capable of industrial application.

We claim:

1. An injectable, stable, sterile aqueous solution of cisplatin in a unit dosage form in a sealed container, said solution being suitable for administration by the injection thereof into man upon the removal thereof from said container, said solution having a concentration of cisplatin between about 0.1 and about 1.0 mgm./ml. and a pH in the range of 2.0 to 3.0.

2. An injectable, stable, sterile aqueous solution of cisplatin in a unit dosage form in a sealed container, said solution being suitable for administration by the injection thereof into man upon the removal thereof from said container, said solution having a concentration of cisplatin between about 0.1 and about 1.0 mgm./ml. and a pH in the range of 2.3 to 2.7.

3. An injectable, stable, sterile aqueous solution of cisplatin in a unit dosage form in a sealed container, said solution being suitable for administration by the injection thereof into man upon the removal thereof from said container, said solution having a concentration of cisplatin between about 0.1 and about 1.0 mgm./ml. and a pH of about 2.5.

4. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.0 to 3.0.

5. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7.

6. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH of about 2.5.

7. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7, said pH being caused by the presence of the appropriate amount of hydrochloric acid, said solution containing in addition a nontoxic, pharmaceutically acceptable, inorganic source of chloride ions in a concentration equivalent to that produced by the presence of sodium chloride in a concentration in the range of 1 to 20 mgm./ml.

8. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7, said pH being caused by the presence of the appropriate amount of hydrochloric acid; said solution containing in addition a nontoxic, pharmaceutically acceptable, inorganic source of chloride ions in a concentration to that produced by the presence of sodium chloride in a concentration in the range of 1 to 20 mgm./ml.; said solution being free of any other added chemical.

9. An injectable, stable, sterile aqueous solution of cisplatin in a unit dosage form in a sealed container, said solution being suitable for administration by the injection thereof from said container, said solution having a concentration of cisplatin of about 1.0 mgm./ml. and a pH in the range of 2.3 to 2.7, said pH being caused by the presence of the appropriate amount of hydrochloric acid; said solution containing in addition a nontoxic, pharmaceutically acceptable, inorganic source of chloride ions in a concentration equivalent to that produced by the presence of sodium chloride in a concentration in the range of 1 to 20 mgm./ml.; said solution also containing a customary, harmless, physiologically acceptable excipient in a concentration in the range of 2 to 150 mgm./ml.

10. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7, said pH being caused by the presence of the appropriate amount of hydrochloric acid; said solution containing in addition sodium chloride in a concentration of about 9 mgm./ml.; said solution also containing mannitol in a concentration of about 10 mgm./ml., said solution exhibiting less than 10% loss of potency as measured by high pressure liquid chromatography upon storage for one month at 56° C.

11. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7, said pH being caused by the presence of the appropriate amount of hydrochloric acid; said solution containing sodium chloride in a concentration in the range of 1 to 20 mgm./ml.

12. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7, said pH being caused by the presence of the appropriate amount of hydrochloric acid; said solution containing sodium chloride in a concentration in the range of 1 to 20 mgm./ml.; said solution being free of any other added chemical.

13. An injectable, stable, sterile aqueous solution of cisplatin in a unit dosage form in a sealed container, said solution being suitable for administration by the injection thereof into man upon the removal thereof from said container, said solution having a concentration of cisplatin of about 1.0 mgm./ml. and a pH in the range of 2.3 to 2.7, said pH being caused by the presence of the appropriate amount of hydrochloric acid; said solution containing sodium chloride in a concentration in the range of 1 to 20 mgm./ml.; said solution also containing a customary, harmless, physiologically acceptable excipient in a concentration in the range of 2 to 150 mgm./ml.

* * * * *